United States Patent [19]

Pless et al.

[11] Patent Number: 4,827,936
[45] Date of Patent: May 9, 1989

[54] APPARATUS FOR STIMULATING THE HEART WITH PROTECTED PACER

[75] Inventors: Benjamin Pless, Palo Alto; Michael Sweeney, Menlo Park; Roger Winkle, Palo Alto, all of Calif.

[73] Assignee: Ventritex, Sunnyvale, Calif.

[21] Appl. No.: 863,181

[22] Filed: May 14, 1986

[51] Int. Cl.⁴ .............................................. A61N 1/36
[52] U.S. Cl. ......................... 128/419 D; 128/419 PG
[58] Field of Search ............ 128/419 D, 419 PG, 421, 128/423

[56] References Cited

U.S. PATENT DOCUMENTS

| | | | |
|---|---|---|---|
| 3,236,239 | 2/1966 | Berkovits | 128/419 D |
| 3,345,990 | 10/1967 | Berkovits | 128/419 PG |
| 3,857,398 | 12/1974 | Dubin | 128/419 D |
| 4,375,817 | 3/1983 | Engle et al. | 128/419 D |
| 4,523,595 | 6/1985 | Zibell | 128/419 D |

Primary Examiner—William E. Kamm
Attorney, Agent, or Firm—Limbach, Limbach & Sutton

[57] ABSTRACT

A combination two-channel defibrillator and programmable pacing stimulator for assesses lethal ventricular tachyarrhythmias and determine defibrillation thresholds during implantable defibrillator procedures. A pair of switching transistors are provided to protect the pacing circuit when a defibrillation shock is delivered. These switching transistors provide symmetric voltage protection and prevent the defibrillation energy from being shunted back to the patient through the pacing leads.

3 Claims, 7 Drawing Sheets

OUTPUT BOARD P1

APPARATUS FOR STIMULATING THE HEART WITH PROTECTED PACER

TECHNICAL FIELD

This invention relates to an apparatus for use in the field of cardiac electrophysiology. More specifically, an apparatus is disclosed for assessing ventricular tachyarrhythmias and determining defibrillation thresholds during implantable defibrillator procedures.

BACKGROUND OF THE INVENTION

In the United States, heart disease is a major health problem. Of the 1.5 million people per year who suffer a myocardial infarction, about 680,000 survive that have ischemia (dead heart tissue) which is the basis for cardiac arrhythmias. Approximately 400,000 people a year die from the most serious types of cardiac arrhythmias.

Arrhythmias can be classified into three broad types. Bradycardia is an abnormally slow heart rhythm. This problem has been successfully treated for a number of years with implantable pacemakers which induce the heart to beat at a faster, normal rhythm. The remaining types of arrhythmias are more difficult to control.

Tachycardia is a rapid cardiac rhythm generally defined as a heart rate greater than 100 beats per minute. There are normal physiologic tachycardias due to exertion or emotion as well as abnormal nonphysiologic tachycardias in which a high rate results in loss of blood pressure. Sustained ventricular tachycardia can result in severe loss of blood pressure, loss of consciousness and can deteriorate into ventricular fibrillation which is fatal if not quickly interrupted.

Fibrillation, unlike tachycardia, is a disorganized cardiac rhythm wherein the heart quivers rather than beats. This quivering is a result of multiple waves of cardiac depolarization spreading and colliding throughout the ventricular tissue. Ventricular fibrillation results in a precipitous decrease in blood pressure followed quickly by brain damage and death.

Arrhythmias are treated using either medication, surgery or implantation of a medical device. Drug therapy is employed initially in the majority of cases and involves the use of various medications to prevent an arrhythmia from starting or being sustained. The main advantage of drug therapy is that no surgical intervention is required. The major drawback to the exclusive use of therapy is the lack of backup therapy to terminate a potentially lethal arrhythmia should the drug eventually fail to prevent the arrhythmia from recurring. Additionally, in attempting to achieve adequate tachycardia prevention, drug related side effects often preclude using an adequate dose of medication.

Surgery involves locating the cause of the arrhythmia and removing or isolating it from the healthy cardiac tissue. The advantage of surgical therapy is that the procedure is curative when successful. The disadvantage of surgical therapy is the morbidity and mortality associated with open heart surgery and the technical difficulty and high cost of the procedure. These factors have restricted the practice of antiarrhythmia surgery.

In 1980, the first implantable defibrillator was implanted in a human patient. Implantable defibrillators sense fibrillation and automatically deliver a high energy pulse. Subsequent studies have indicated that these devices are effective in preventing sudden death from fibrillation. Presently, no single implantable device has been developed to control all three types of arrhythmias.

The analysis of patients who have arrhythmias often requires invasive testing in an electrophysiology lab. This invasive testing is carried out in a variety of situations. For example, invasive testing is common during a selection process used to determine which patients might be candidates for implantable defibrillators. Invasive testing is also utilized in trying to assess and characterize tachycardia which is then treated with drugs. In any case, in the testing process, catheters are inserted into the heart and the patient's arrhythmia is provoked with programmed electrical stimulation. When the arrhythmia manifests itself, the physician attempts to terminate it with antitachycardia pacing. Antitachycardia pacing is described in the literature and consists of a series of low voltage pulses designed to reset the normal heartbeat. If pacing fails, the patient is either cardioverted with a substantially higher voltage shock or defibrillated with a very high voltage energy pulse.

Low energy cardioversion utilizes pulses with energy levels far greater than pacing pulses but lower than high energy defibrillation pulses. With energies of less than 5 joules, this mode of therapy is based on the theory of interrupting the arrhythmia by stimulating the tissue, rendering it nonexcitable. Low energy cardioversion has been clinically demonstrated as effective. Its drawbacks include patient discomfort and the fact that improperly timed pulses can accelerate tachycardias and occasionally induce fibrillation.

In contrast, high energy defibrillation uses pulses with energy levels tens of thousands of times greater than pacemaker pulses. High energy defibrillation is accomplished by stimulating a large portion of the ventricular tissues simultaneously and rendering it nonexcitable, thereby terminating the arrhythmia. If a patient is found suitable, an internal defibrillator can be implanted to control the arrhythmia. During the operation, the patient's defibrillation threshold must be determined. First, the patient is fibrillated using a programmable stimulator, then a special defibrillator is used to determine the energy required to defibrillate the patient.

The invention described herein facilitates the assessment of arrhythmias and defibrillation thresholds resulting in improved patient care and substantially decreased patient risk. In the prior art, there existed both programmable stimulators and cardioversion/defibrillator devices. The programmable stimulator includes a means to pace the patient's heart with critically timed stimuli to provoke the cardiac arrhythmia. These devices are then used to terminate the arrhythmia using antitachycardia pacing. If the pacing accelerates the arrhythmia or fails to terminate it, then a standby defibrillator device must be set up and the patient cardioverted or defibrillated. Frequently, the patient is cardioverted or defibrillated externally. More recently, internal catheters have been provided to deliver the defibrillation shock.

As noted above, an external cardioverter/defibrillator is used during implantable defibrillator procedures to assess the patient's cardioversion/defibrillation threshold. When the patient is fibrillated using a programmable stimulator, the unit must be disconnected before a test defibrillation pulse can be applied. Frequently, the test pulse fails to defibrillate the patient. Once the physician recognizes the failure to defibrillate, he must program a new, higher voltage rescue shock into the defibrillator. The unit must then recharge prior to delivery of the rescue shock. This procedure takes considerable time and there is ample opportunity for operator error. Any delay in defibrillating the patient is a serious health risk and improving the response time to the delivery of the rescue shock substantially reduces patient risk. Accordingly, it would be desirable to eliminate any unnecessary time between delivery of the test shock and rescue shock.

In the above described procedures, it is also clear that in the electrophysiology lab, it is frequently necessary to use both a programmable stimulator and a cardioverter/defibrillator. Present day equipment requires the operator to switch leads and move back and forth between two pieces of equipment. During this procedure, care must be taken to prevent any of the high voltage charge delivered by the defibrillator from reaching the output leads of the programmable stimulator to avoid damaging the latter. Accordingly, it would be desirable to provide a single combination test unit wherein leads would not have to be changed and automatic protection of programmable stimulator would be provided.

Another drawback of the defibrillation devices available in the prior art relates to the fact that little or no measurement and visual feedback is given to the surgeon regarding the defibrillation pulse. More specifically, the surgeon typically sets a pulse width and a voltage level for a test shock. If this test shock fails, the surgeon cannot be sure whether it was the result of shorted leads, an unexpectedly high resistance in the heart or whether the voltage was just too low to stop the defibrillation. There presently exists some low voltage pacing devices which have been designed to provide additional information to the surgeon regarding patient resistance and energy delivered. However, to date, no systems have been provided to calculate and display this information in a defibrillation setting. In a life-threatening situation, such as cardiac fibrillation, such information is extremely important and can aid the surgeon in assessing the type of rescue shock necessary to end the fibrillation.

The energy delivered to the heart of a patient is generally measured in joules. The energy level of the shock is analogous to a dosage in therapy. In prior art devices, as in the subject invention, the surgeon sets the defibrillation shock by adjusting a voltage level and the pulse width. However, in the prior art devices, no information is given to the physician as to the energy which will be received by the patient if a shock with those set parameters were delivered. Therefore, it would be desirable to provide a device which displays the estimated energy based on the set voltage level and pulse width.

Accordingly, it is an object of the subject invention to provide a new and improved apparatus for electrophysiology testing in patients suffering from severe ventricular arrhythmias.

It is another object of the subject invention to provide a new and improved apparatus which advantageously combines a programmable stimulator and an internal cardioversion/defibrillation device.

It is a further object of the subject invention to provide a combination stimulator/defibrillator apparatus with automatic circuit protection for the stimulator.

It is a still another object of the subject invention to provide a new and improved defibrillator which includes a pair of capacitor banks permitting the simultaneous storage of both a test shock and a rescue shock.

It is still a further object of the subject invention to provide a new and improved defibrillator apparatus which includes automatic recharge circuitry to reduce the time necessary to deliver a rescue shock during an emergency procedure.

It is still another object of the subject invention to provide a new and improved apparatus which allows multiple, independent entries of data which are stored for later recall during testing procedures.

It is still a further object of the subject invention to provide a new and improved defibrillator apparatus which will display measurement of resistance and energy delivered during a defibrillation shock.

It is still a another object of the subject invention to provide a new and improved defibrillator apparatus which will display the energy which is estimated to be delivered if a shock of a given voltage and pulse width is to be delivered.

SUMMARY OF THE INVENTION

In accordance with these and many other objects, the subject invention provides a single device that can be used in electrophysiology labs during ventricular tachycardia procedures. The invention integrates an innovative two-channel defibrillator with a programmable stimulator in a manner that enhances response time to the patient and provides more information to the surgeon. A number of new features have been included which address unique problems encountered when treating severe arrhythmia.

In use, an indwelling defibrillating catheter with pacing capabilities is inserted into the heart. In this manner, the arrhythmia can be induced by the subject apparatus and, if necessary, the patient can be defibrillated within seconds of the initiation of the arrhythmia. In accordance with the subject invention an automatic interrupt means is provided to protect the delicate circuits of the stimulator from the high voltage discharge delivered by the defibrillator without shunting current to the patient.

Another advantage of the unique combination found in the subject invention is that the time necessary to initiate defibrillation is much shorter than is currently possible, resulting in decreased patient risk. To enhance the rapidity of defibrillation, the unit always remains charged to the programmed defibrillating voltages.

Devices which exist in the prior art all have a charge button that must be pressed to initiate the charging of the storage capacitors. This feature was generally provided because the devices were subject to false triggering wherein the high voltage would be released inadvertently. In recent years, more reliable equipment has been developed which is not subject to false triggering. Nonetheless, the prior art devices still incorporate both a charge button (which is depressed to load the capacitor ) and a separate switch, which must be subsequently depressed, to the deliver the shock after the capacitor has been charged. In the emergency situation of a patient fibrillation event, the additional step of having to press a charge button can be delayed or overlooked. Even if the charge button is properly pressed, time will elapse before the capacitor bank is raised to the level of the desired shock. In the subject invention, the charge button is eliminated and an automatic circuit is provided to maintain the capacitor banks at the set voltage level.

The defibrillation circuitry of the subject apparatus includes two independent channels. Each channel includes its own storage capacitors which can be independently programmed. Prior to a surgical procedure, the surgeon can program one channel with a test shock and the other channel with a much stronger, rescue shock.

The independent capacitor arrays will automatically be charged to these two independent levels.

In the lab, the test shock can be used to attempt defibrillation. If this test shock does not revert the fibrillation, the rescue shock can be delivered immediately. This is in sharp contrast to any existing device where 20 or 30 seconds might elapse before a rescue shock can be applied.

A memory capability is also provided to instantly change the program settings of the two defibrillation channels to previously selected values. Since the charging of the high voltage capacitors is automatic, this provides an effective way to quickly change to a maximum energy setting if the initial two shocks fail to defibrillate the patient. A similar memory capability is included in the programmable stimulator. By this arrangement, when the electrophysiologist induces the patient's arrhythmia he can instantly go to a previously selected set of antitachycardia pacing parameters and thereby attempt to terminate the arrhythmia without the delay of further programming.

As noted above with the prior art devices, if a test shock fails to defibrillate the patient, there is no information presented to the physician to help him alleviate the problem. The subject invention provides a means to calculate and display such information. More specifically, in conjunction with each defibrillation shock, the unit will display to the physician the actual energy, measured in joules, delivered to the patient, as well as the patient's electrical resistance. If the resistance is abnormal, this could indicate a problem with the electrode system. Without the displayed information, a physician might not be alerted to the problem thereby compromising patient's safety. In a preferred embodiment, the residual charge of the capacitor is measured and is used to calculate the energy delivered and patient resistance.

As another aid to the physician, the subject invention also provides a means for calculating and displaying the energy which is estimated to be delivered during a defibrillation shock. The energy delivered will vary based on a variety of parameters, such as the voltage level, pulse width and patient resistance. All of these parameters are used by the apparatus to calculate the expected energy to be delivered. By this arrangement, the physician can best gauge the proper voltage and pulse width settings needed to deliver the desired energy level shock.

Further objects and advantages of the subject invention can be appreciated by referring to the following detailed description taken in conjunction with the drawings in which:

DETAILED DESCRIPTION OF THE PREFERRED EMBODIMENT

Figure 1:
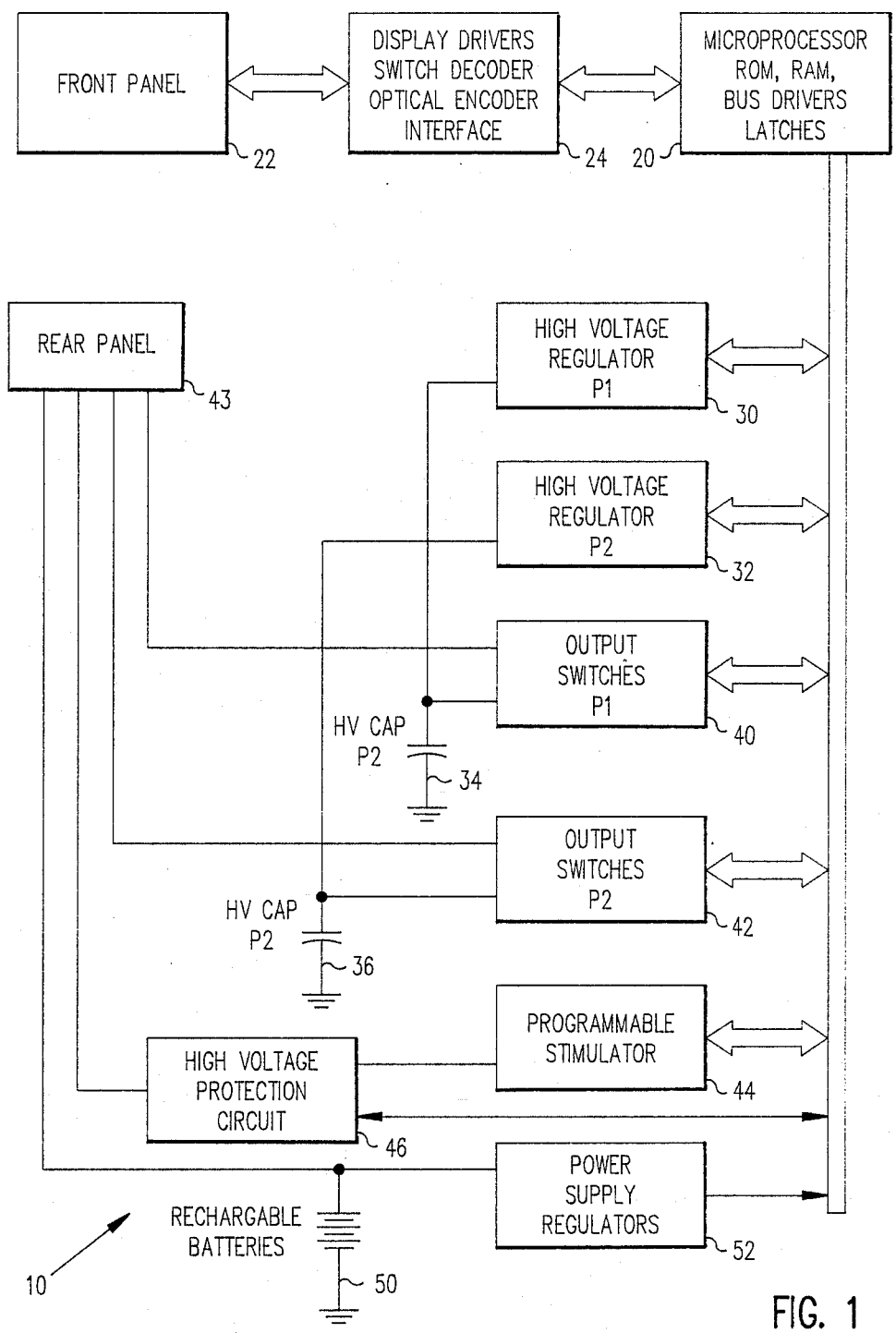
FIG. 1 is a system block diagram of the apparatus of the subject invention.

Referring to FIG. 1, there is illustrated a system block diagram of the apparatus 10 of the subject invention. The apparatus 10 is microprocessor controlled. In the preferred embodiment, 68HCII microprocessor, manufactured by Motorola, is used.

A microprocessor board 20 includes standard components, such as a program ROM, RAM, bus drivers and latches. The front panel 22, which will be discussed in greater detail below, interfaces with the microprocessor board 20 through a support board 24. Support board 24 includes display drivers, switch decoders, an optical encoder, and other standard interface circuits. The microprocessor writes information to the display drivers and receives information through the optical encoder and switch matrix interfaces. The elements in boards 20 and 24 are standard and any suitable alternatives can be utilized.

The subject apparatus includes six other principal boards which communicate with the microprocessor. A pair of high voltage regulator boards 30 and 32 are programmed by the microprocessor to charge the high voltage capacitors 34 and 36 to the voltage entered on the front panel 22 by the physician. Details of the high voltage regulators will be discussed below with reference to FIGS. 5 and 6. After defibrillation, data is read back from the regulator boards that contain information on energy delivered and the patient's electrical resistance. This function will be discussed below with reference to FIG. 8.

Output boards 40 and 42 include high voltage electrical switches to connect patients to the high voltage energy storage capacitors through the rear panel 43 for the duration selected on the front panel 22 by the physician. The output boards will be discussed in greater detail in conjunction with FIG. 11.

The subject apparatus further includes a programmable stimulator board 44. The programmable stimulator board also interfaces with the microprocessor 20 to generate the pulses that are programmed into the front panel by the physician. A more detailed description of the programmable stimulator board will be made with reference to FIG. 12.

During a defibrillation attempt, the output from the programmable stimulator is protected through a circuit on board 46. If this protection were not available, the output of the stimulator 44 could be easily damaged. A more detailed description of the protection circuit will be made with reference to FIG. 10.

The apparatus 10 is powered by a 12 volt rechargeable battery 50 connected to a power supply regulator board 52. Board 52 regulates the system power supply and provides a signal to the microprocessor board when the batteries need recharging.

The operation of the subject apparatus 10 will be described now with reference to the front panel inputs shown in FIG. 2 along with various accompanying flow charts where necessary. In the preferred embodiment, the front panel includes an array of LCD displays, pushbutton switches and an optical encoder 60. The basic operation calls for the physician to depress the switch next to the parameter he wants to adjust. The selected switch lights up indicating that the optical encoder 60, labelled "parameter adjust", will control the associated parameter. By rotating the knob 60, the parameter next to the lighted switch will be varied. As can be seen from FIG. 2, the left portion of the front panel controls the defibrillator operation, while the right portion controls the programmable stimulator.

Figure 3:
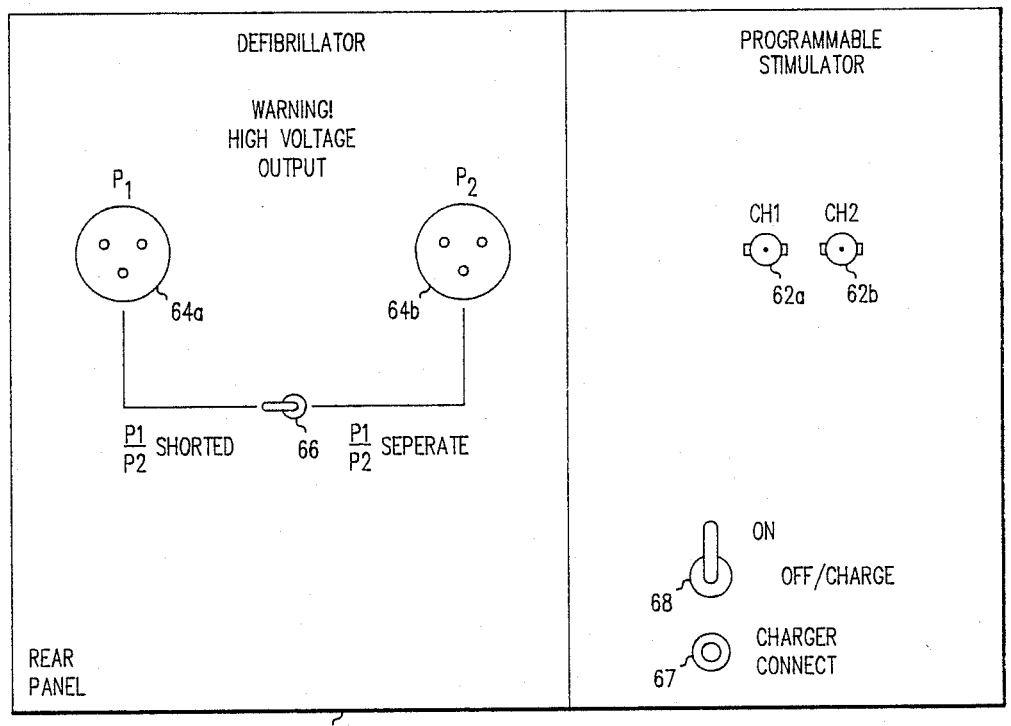
FIG. 3 is a diagram of the rear panel of the apparatus of the subject invention.

All electrical hookups are routed to the rear panel 43 as shown in FIG. 3. The two channels of the programmable stimulator terminate in standard BNC connectors 62A and 62B (labelled CH1 and CH2). Used separately, pacing pulses can be delivered to different parts of the heart, although the outputs may be ganged together.

The high voltage outputs 64A and 64B, (labelled P1 and P2) are high voltage connectors which can be left separate or can be shorted together using a toggle switch 66. When the outputs are shorted together, the output from both channels is delivered through the P1 output. FIG. 3 also shows an input 67 to receive a charge line to recharge the storage batteries. The charger is controlled by switch 68.

In order to deliver the P1 shock, the physician refers to the LCD display block 69, labelled "OUTPUT" on the front panel. As illustrated in FIG. 2, P1 has been selected and is displayed in block 69. If P2 is displayed and the physician wants P1, he can press the output switch to toggle to P1. The "parameter select" switch below the output switch will be discussed in greater detail below.

After the P1 shock has been selected, the electrophysiologist can verify that the voltage and pulse width are correct. This information is displayed in the top display block 70 of FIG. 2. As discussed above, these parameters can be adjusted by depressing the associated switch and rotating the encoder knob 60. If the parameters are changed, an automatic charging circuit discussed below will adjust the voltage in the capacitor bank to the proper level. When charging is complete, a ready light 72 will be illuminated, indicating that the charge can be delivered.

In accordance with the subject invention, prior to initializing a test procedure, a second, rescue shock can also be programmed. In this case, the surgeon would also adjust the parameters for the P2 shock. In the illustrated embodiment, the parameters are shown in display block 74. In a typical situation, as illustrated herein, the second rescue shock will have significantly greater voltage and a longer pulse width since it would be assumed that the first defibrillation shock failed to revert the fibrillation.

In use, the patient can be defibrillated by pressing the deliver switch 76 which will deliver the voltage stored in the P1 capacitor 34. If this shock fails to defibrillate the patient, the "OUTPUT" button is depressed causing the associated display to toggle to P2. The deliver button is then depressed and the energy in capacitor 36 will be immediately delivered.

Figure 4:
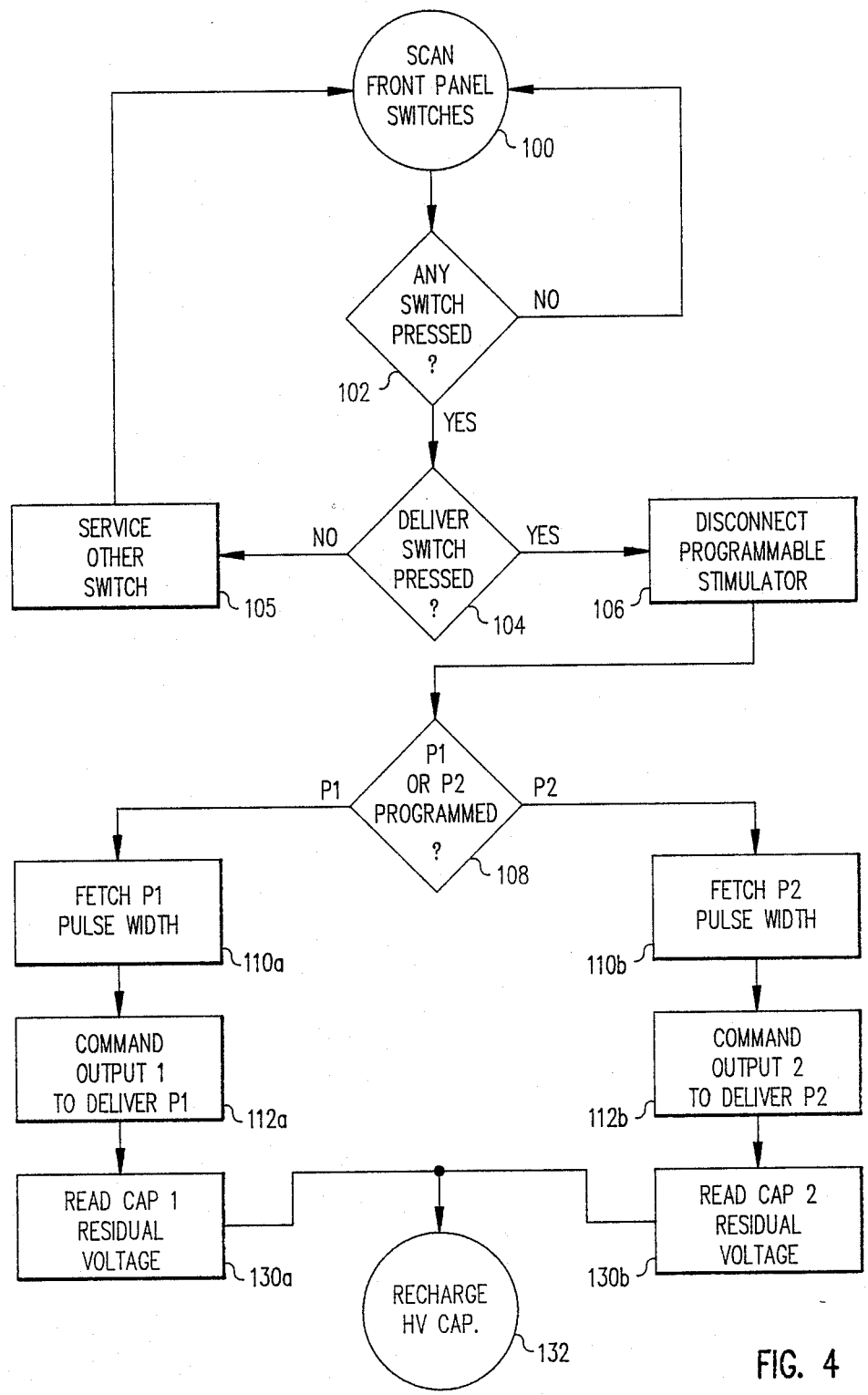
FIG. 4 is a flow chart illustrating the steps of delivering high voltage defibrillation shocks.

FIG. 4 is a flow diagram that describes the software in the microprocessor used to deliver the P1 and P2 charges. As shown therein, the front panel switches are continually scanned in steps 100 and 102. If any switch is pressed, priority is given to the deliver switch in step 104. If the deliver switch has not been depressed, the other switches will be serviced in step 105. If the deliver switch 76 is depressed, the outputs of the programmable stimulator will be protected via the disconnection step 106.

Figure 10:
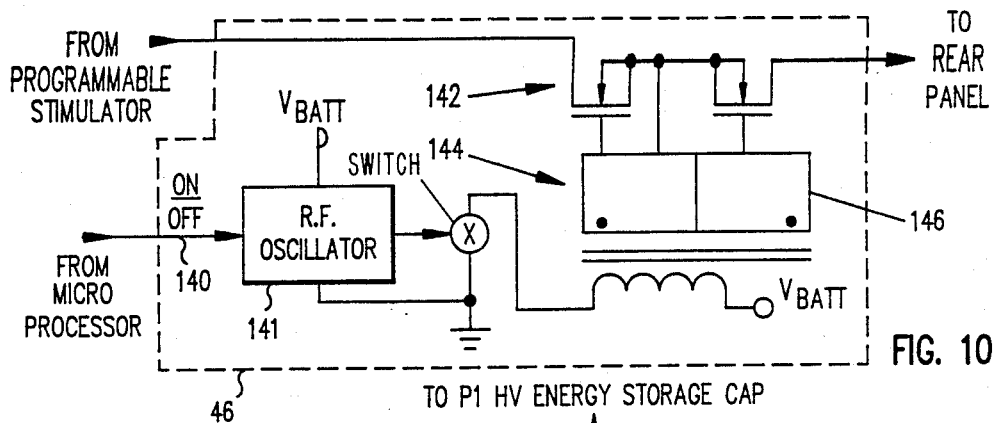
FIG. 10 is a schematic diagram of the high voltage protection circuit.

The circuit 46 for disconnecting and protecting the programmable stimulator is shown in FIG. 10. Any signals from the stimulator must pass through this circuit before reaching the rear panel. Normally, the microprocessor leaves this circuit on by setting the ON/OFF line 140 to the RF oscillator 141 high.

Figure 12:
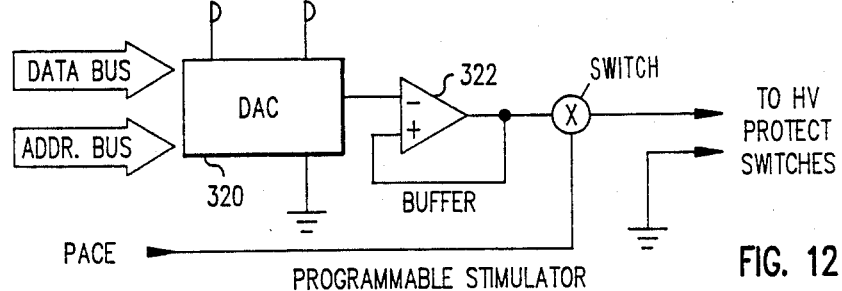
FIG. 12 is a schematic diagram of the programmable stimulator.

The RF oscillator 141 couples energy to the gates of the high voltage switches 142 (Motorola MTM5N100 MOSFETs) through a small pulse transformer 144. To turn the switches 142 off, the microprocessor sets the ON/OFF 140 line low, disabling the RF oscillator. The source-to-source connection of the MOSFETs along with the transformer isolation of the gate drives 146 results in a symmetric (+,−) 1000 volt protection. In this arrangement, the high voltage from the defibrillator pulse is not shunted back to the patient through the pacing leads since the disabled MOSFETs define an open circuit. This approach is therefore superior to a more simple shunt circuit, such as a Zener diode placed across the pacing leads. In the latter circuit, the stimulator would be protected, but the high voltage would be shunted to the pacing leads such that the characteristics of the defibrillation shock delivered would change, which can reduce efficiency and could damage heart tissue. The ground line from the programmable stimulator also goes through a set of protection switches to avoid defibrillation current shunting during high voltage output, as shown in FIG. 12.

After the programmable stimulator is disconnected, the front panel parameters are checked in step 108 and the proper pulse width for the associated pulse is selected in steps 110A or 110B of FIG. 4. The microprocessor then commands the appropriate output board to connect the patient to the previously charged high voltage capacitor in step 112A or 112B.

Figure 11:
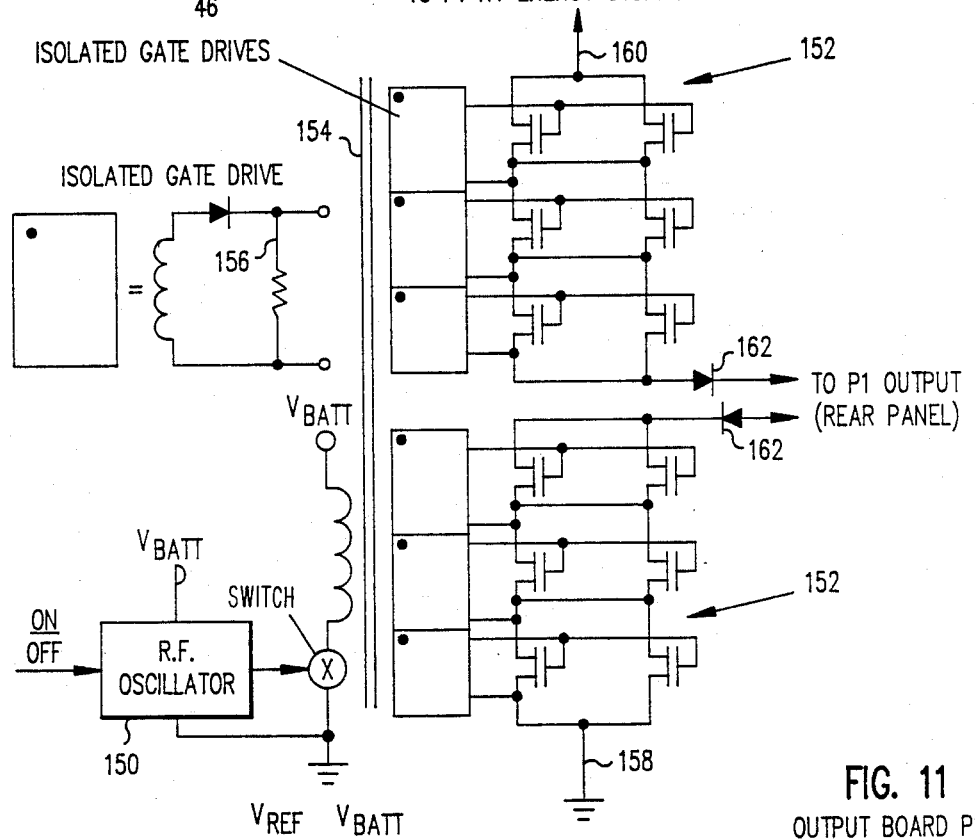
FIG. 11 is a schematic diagram of the high voltage output circuit.

FIG. 11 is a block diagram of the output board 40 for capacitor P1. To deliver a defibrillation pulse the microprocessor turns on the RF oscillator 150 for the programmed duration. The series-paralleled IGFETs 152 (Motorola MTP20N50) provide a 50 amp drive capability with low output leakage. While the RF oscillator 150 is on, the transformer 154 couples a square wave of voltage from its primary to its secondary. This voltage is rectified, and held by the gate capacitance of the IGFETs. When the RF oscillator is turned off, a pull down resistor 156 discharges the gate capacitance turning off the IGFETs. When the IGFETs are on, the ground connection is made to the patient through lead 158, and the high voltage capacitor is connected through the other lead 160. The current is led through high voltage diodes 162 in series with the patient. The diodes provide reverse voltage protection for the IGFETs.

After the charge has been delivered and prior to the automatic recharging of the capacitor 36, the residual voltage on the capacitor is measured in step 130A or 130B. In the preferred embodiment, residual voltage is measured to permit the calculation of resistance and energy delivered to the patient as discussed in greater detail below. After the residual voltage has been measured, the capacitor is automatically recharged in step 132 shown in FIGS. 4 and 5.

As can be appreciated, by having two independent programmable capacitor arrays, a test shock and a rescue shock of different voltages can be delivered with virtually no time delay therebetween. In use, the physician will observe whether the test shock has succeeded in defibrillating the patient and if that has failed, a second, higher voltage rescue shock will be delivered.

Another unique aspect of the subject invention which reduces the time necessary to respond to a critical situation concerns the automatic recharging of the capacitors. As noted above, all prior art devices required that the voltage be set and thereafter a charge button be pressed to raise the capacitor bank to the desired level to avoid false triggering problems. In applicant's invention, as soon as the parameters are entered into the device, both the capacitor banks 34, 36 will be charged to their set levels. In addition, as soon as a shock is delivered, and after the residual voltage has been read, the capacitors will begin to immediately recharge.

Figure 5:
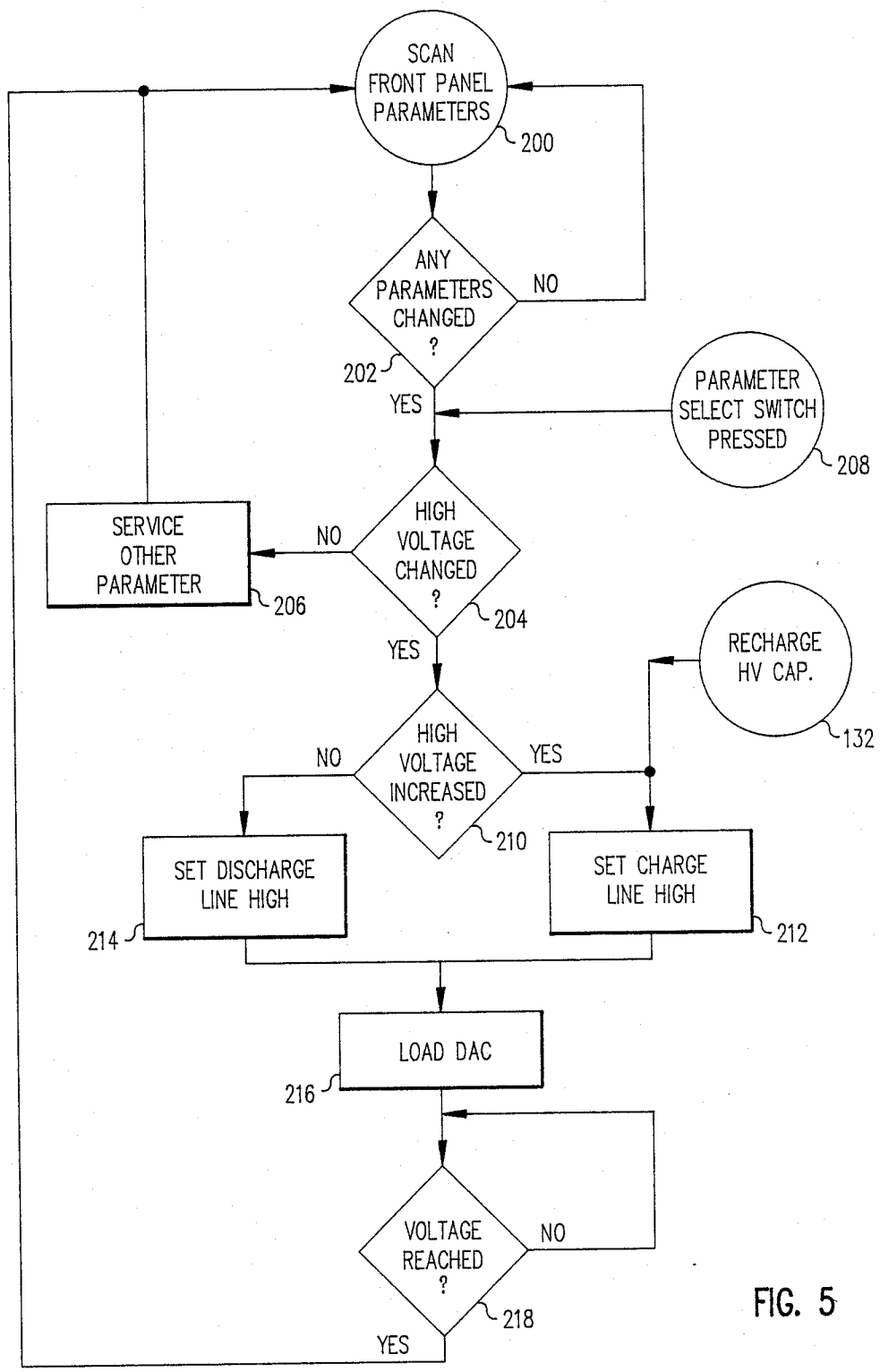
FIG. 5 is a flow chart illustrating the automatic charging feature of the subject invention.
Figure 6:
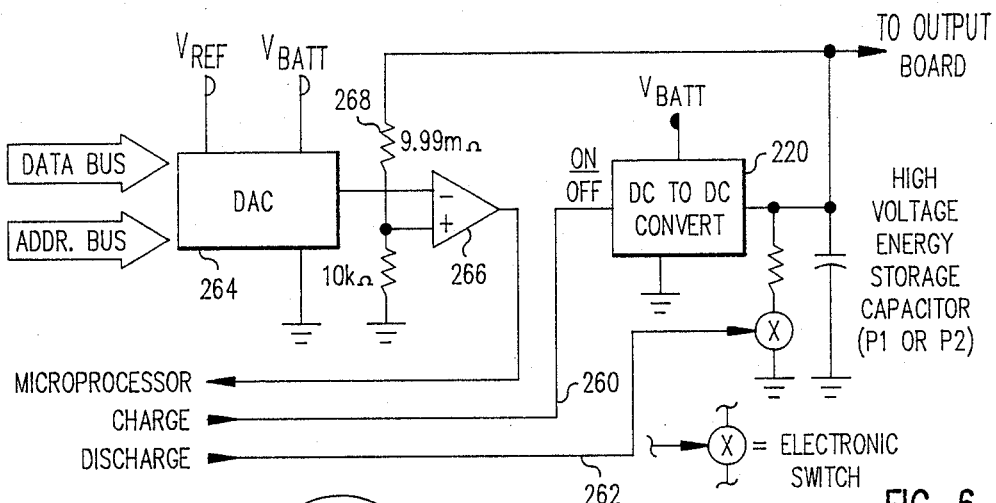
FIG. 6 is a schematic diagram illustrating the high voltage regulator used to control and measure the energy in the storage capacitors.

The steps taken by the microprocessor to carry out this automatic charging are shown in FIG. 5 and the regulator circuit itself is shown in FIG. 6. As shown in FIG. 5, the front panel parameters are continuously scanned in steps 200 and 202. If any parameters have been changed, the microprocessor will determine if the high voltage (P1 or P2) parameter has changed as shown in step 204. A change in the high voltage parameter could result from data entered via the optical encoder 60. The setting could also be changed as a result of pressing the parameter select switch 80A and will be discussed below. In any event, if the high voltage parameter has not changed, the other switches will be serviced as shown in step 206. If the high voltage parameter has changed, the processor will determine if it has increased in step 210.

If the high voltage parameter has increased, the capacitor will be charged, while if the parameter has been decreased, the capacitor will be discharged. As shown in FIG. 5, if the capacitor has been discharged by delivering its energy to the patient, the processor will instruct the regulator board to charge the capacitor as indicated by the input 132, also shown in FIG. 4.

If the capacitor is to be charged, charge line 260 on the regulator board shown in FIG. 6 will be set high. If the capacitor is to be discharged, discharge line 262 will be set high. In conjunction with setting the charge or discharge lines, the microprocessor will also load the voltage read from the selected switch (P1 or P2) into the digital to analog converter (DAC) 264 in step 216. A comparator 266 compares the high voltage from the storage capacitor (P1 or P2) to the output of the DAC 266. Note that the output from the capacitor bank is divided down through a resistor array 268 prior to entering the comparator.

The output of comparator 266 is fed back to the microprocessor which detects when the output of the capacitor matches the output of the DAC 266 in step 218. The charging or discharging is then halted. As seen in the circuit diagram of FIG. 6, where the capacitor is being charged, low voltage from battery $V_{BATT}$ is supplied to a low to high voltage DC to DC converter 270 to charge the storage capacitor.

As pointed out above, another unique advantage of the subject invention is the ability of the microprocessor to store a number of preset parameters. In this manner, the physician can program all the necessary parameters prior to initiating the surgical procedure. This ability is provided in both the programmable stimulator and defibrillator sections of the apparatus. As illustrated in the front panel in FIG. 2, both sides of the display include "SELECT" buttons 80A and 80B. By pressing either button, the display and electronics toggle between parameter set A and parameter set B. Each parameter set is independently adjustable and all the information is retained in the RAM on the microprocessor board 20.

Figure 7:
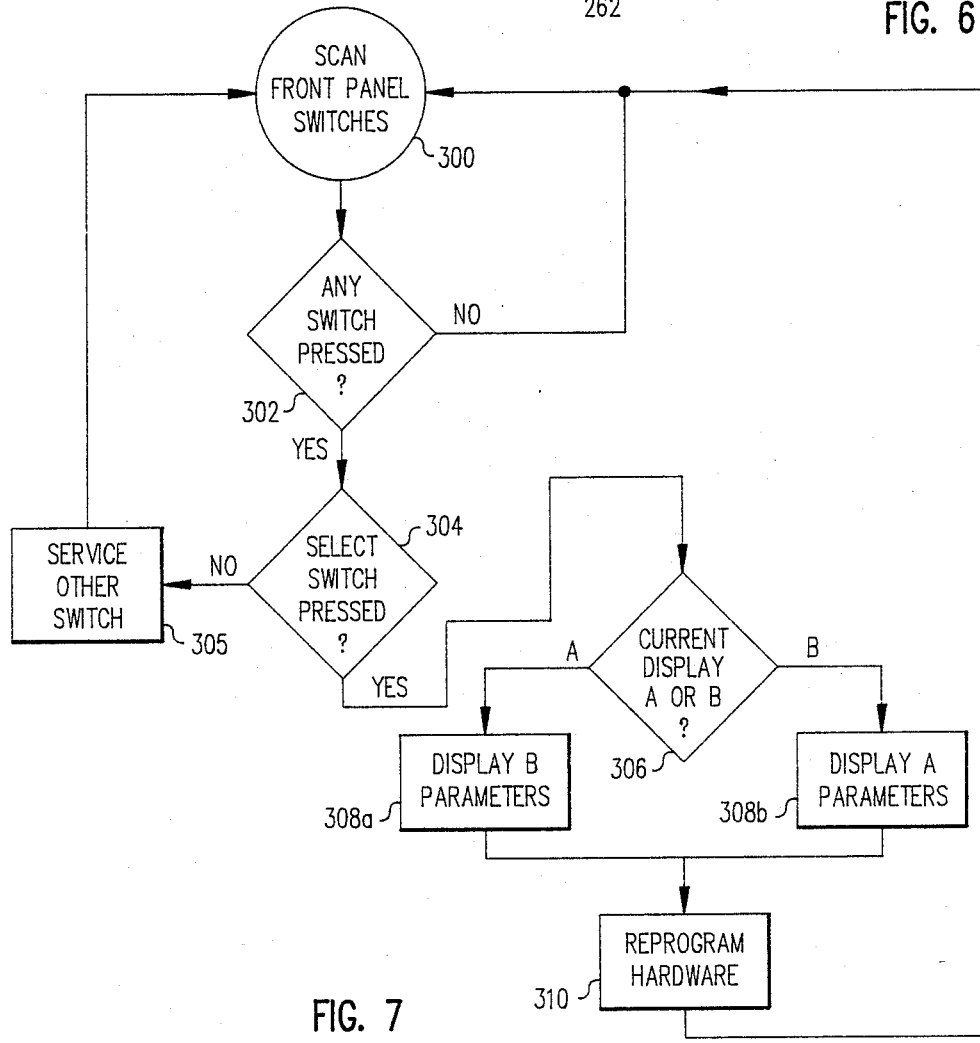
FIG. 7 is a flow chart illustrating the ability to display alternate parameters which are stored in memory.

The steps taken by the microprocessor in relation to this selection process are shown in FIG. 7. More particularly, the front panel switches are scanned in steps 300 and 302. If a switch other than the select switch 80 is pressed, as determined in step 304, the other switches will be serviced as shown in step 305. If a select switch 80 has been pressed, the microprocessor determines what is currently being displayed in step 306. This current display is then changed in step 308A or 308B to the alternate set of parameters.

The microprocessor also functions to reprogram the hardware in step 310. Thus, for example, in the defibrillator section, the voltages in the capacitors will be reprogrammed to the new P1 and P2 voltage levels. The recharging will be automatic, enabling the physician to respond quicker to a particular situation.

It should be noted that the combination of the multiple storage parameters as well as the automatic charging feature and two channel capacitor array interact to improve patient care. More particularly, if a patient has gone into fibrillation, the physician can deliver a P1 pulse from parameter set A as a test shock. As soon as that shock has been delivered, the P1 capacitor begins recharging. If a surgeon determines that the first shock was insufficient to revert the fibrillation, the P2 shock from parameter set A can be given. If the P2 shock is also insufficient to revert the fibrillation, the physician can then select parameter set B. As noted above, prior to this selection the capacitors would already be recharging. The device would then have to merely complete the automatic recharging of the capacitors to the new levels of parameter set B and then the ready light will illuminate, permitting the physician to deliver a third shock. In the prior art devices, 20 or 30 seconds elapsed between each successive shock, whereas in the subject invention, this time period can be significantly reduced.

The ability to enter and store two sets of parameters is also advantageous when using the programmable stimulator. As illustrated in block 84 of FIG. 2, a series of pulses have been programmed as parameter set A. As seen in block 85 all the pulses are programmed to have a 4.8 volt amplitude and a 0.45 millisecond pulse width. The parameter set A pulse series includes 8 pulses, each spaced 500 milliseconds apart (S1) followed by another pulse in 450 milliseconds (S2). The channel 2 pulses (which may be sent along the channel 1 line to the same spot in the heart) provide two more pulses each spaced apart at 400 and 350 milliseconds, respectively. This sequence is a typical of one intended to induce a tachycardia episode.

Parameter set B can be programmed to have a series of pulses designed to revert the tachycardia. For example, a group of eight, similar pulses, spaced apart 300 milliseconds can be used to try to revert the tachycardia. The exact pulse train which is used to revert the tachycardia will vary based upon the patient. It should be noted, however, that the subject invention allows the physician great flexibility in programming the pulses.

Furthermore, if the intended reversion pulses fail, the surgeon can immediately deliver a defibrillation pulse from the same device along the same leads. As noted above, in this case, the programmable stimulator leads will be automatically disconnected, preventing damage.

Figure 2:
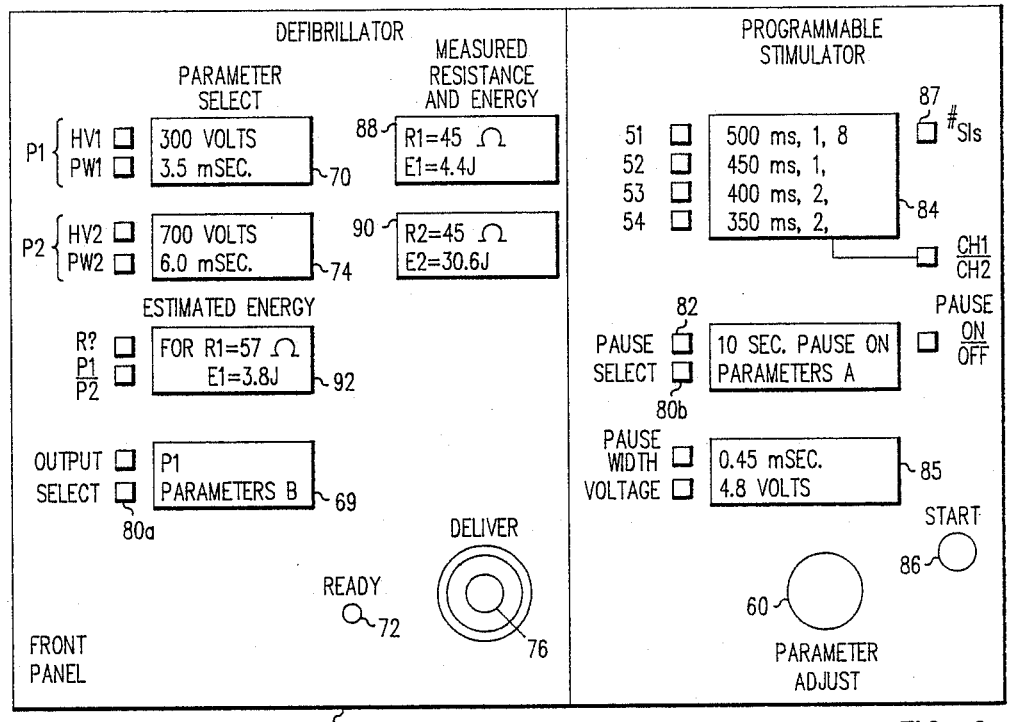
FIG. 2 is a diagram of the layout of the front panel of the apparatus, illustrating the various input systems and displays.

The subject apparatus is also provided with a "PAUSE" switch 82 shown on the front panel in FIG. 2. When this switch is off, the series of pulses in block 84 will be delivered once, each time the start button 86 is depressed. If the pause switch is on, the series will be delivered repeatedly, every 10 seconds, giving time for the physician to alter the parameters in block 84 between each delivery. In this way, small changes can be made until a tachycardia is induced. Switch 87, labeled "S1", is used to set the number of S1 pulses which will be delivered.

FIG. 12 is a simplified block diagram of the programmable stimulator. In operation, the microprocessor writes the desired pacing voltage to a DAC 320 in HEX format. The output of the DAC is buffered with an op-amp follower circuit 322 to increase its output current drive capability. When the START button 86 is pressed, the microprocessor paces the heart by sending a pulse of the programmed width (as selected on the front panel) to the PACE line 324. The pulse width is timed using the timer built into the 68HC11 microprocessor. After timing the first pulse, the microprocessor times the programmed pulse-to-pulse interval (500 msec for S1, as shown on the front panel; 450 msec for S2; etc.). After each pulse-to-pulse interval, the microprocessor stimulates the heart by activating the PACE line for the programmed pulse width.

As described above, when defibrillating a patient, it is advantageous to provide the physician with information regarding the patient's resistance and the energy delivered by the pulse. This information is displayed in the front panel shown in FIG. 2 in blocks 88 and 90. This information could be derived, for example, by measuring the current delivered during defibrillation and then calculating the energy and resistance. In the preferred embodiment, energy and resistance are calculated by measuring the residual voltage on the discharge capacitor, as noted in step 130 of FIG. 4.

Figure 8:
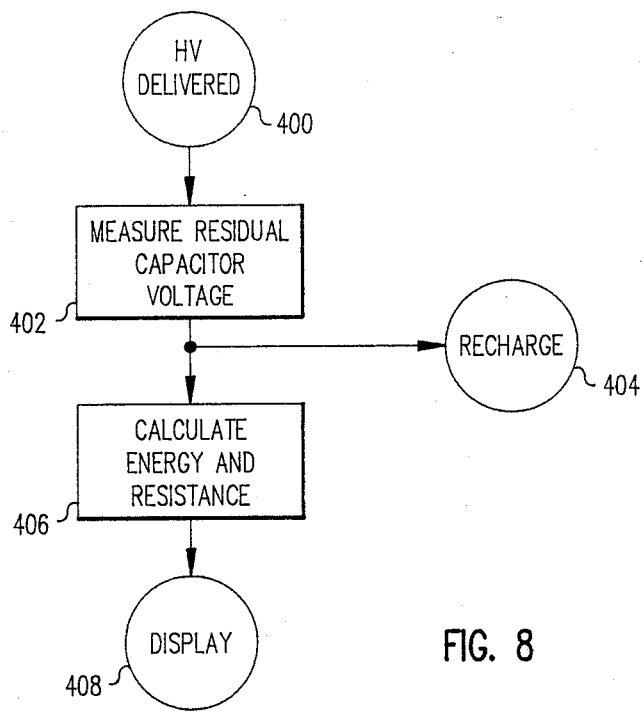
FIG. 8 is a flow chart illustrating the steps used to calculate and display energy and resistance.

Referring to FIG. 8, the steps taken by the microprocessor for calculating and displaying energy and resistance are illustrated. More specifically, after the high voltage is delivered in step 400, the residual voltage on the capacitor is measured.

The residual voltage on the capacitor is measured by setting to low both the charge and discharge lines 260, 262 on the regulator board shown in FIG. 6. The residual voltage of the capacitor will be supplied to the positive lead on the comparator 266. The microprocessor then varies the output of the DAC 264 in a successive approximation fashion. More specifically, if the voltage output from DAC 264 is higher than the input from the capacitor, the comparator output will be low and the microprocessor will drop the voltage output of the DAC. If the new output from the DAC is not low enough to change the output from the comparator, further reductions in the output will be made until the comparator output toggles to high. Then the voltage from the DAC will be increased until the comparator output toggles back to low. This procedure will continue until a change in the least significant bit of the code to the DAC is enough to toggle the output of the comparator. At this point the code in the DAC represents the residual voltage on the capacitor voltage.

After the residual voltage on the capacitor is measured, the microprocessor begins the recharging procedure 404 as discussed in detail with regard to FIGS. 5 and 6. The microprocessor will also calculate the energy and resistance delivered in step 406.

The energy delivered in the shock can be calculated using the following equation:

$$J = 0.5C(Vi^2 - Vf^2) \tag{1}$$

where Vi equals the initial voltage, Vf the residual voltage, C the capacitance of the high voltage capacitor, ad J the energy delivered in joules.

Resistance R can be calculated by the following equation:

$$R = -PW/[(C) \ln(Vf/Vi)] \tag{2}$$

when PW is the pulse width of the defibrillating shock. The energy and resistance are then displayed on the front panel as shown in step 408 and illustrated in FIG. 2 in blocks 88 and 90.

By supplying the physician with the measured resistance and energy, intelligent decision making can be carried out regarding subsequent energy pulses. Clearly, if the resistance is much less than expected, it would indicate a short in the leads. In addition, a physician can note the actual energy delivered when preparing to deliver another shock at this or a subsequent point in time.

As seen from FIG. 2, the front panel also includes a display block 92 for illustrating the estimated energy. This display is intended to supply the physician with information about the expected energy to be delivered if the pulse that is presently selected on the LCD output of the panel were to be delivered. In order to make this calculation, the physician must enter the expected resistance of the patient. Prior to any testing, this resistance will be set to a standard level. After some initial testing, the physician may be able to provide a more accurate number for this resistance.

Figure 9:
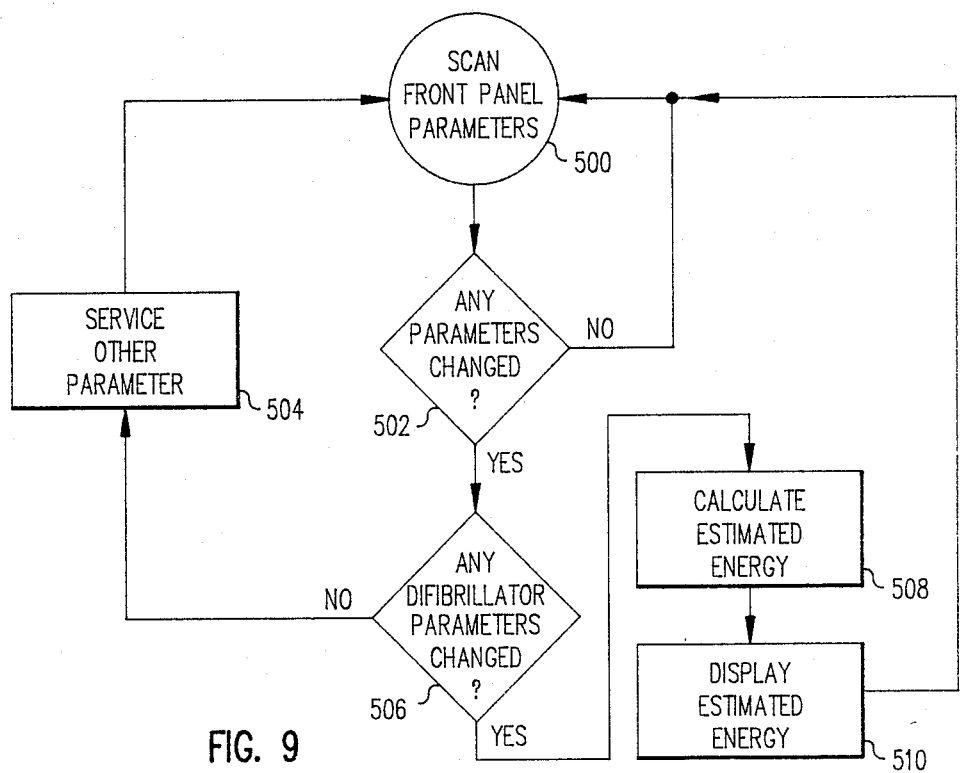
FIG. 9 is a flow chart illustrating the steps used to calculate and display of estimated energy.

FIG. 9 illustrates the steps taken by the microprocessor to carry out this function. As in the previous flow diagrams, the microprocessor will scan the front panel parameters in steps 500 and 502. If none of the defibrillator panel switches have been changed, the other parameters switches can be serviced in step 504. However, if any of the defibrillator panel switches have been changed, a new estimated energy must be calculated. Note that any change entered by the physician to the expected resistance, pulse width or voltage level will initiate the calculation of a new estimated energy. The calculation of the estimated energy takes place in step 508.

The estimated energy can be calculated by using Equation (1) above where Vf (which was previously the residual voltage measured on the capacitor) is now approximately $$Vf = (Vi)\exp[-PW/RC] \tag{3}$$

The variables listed above are the same as those discussed with relation to the display of actual resistance and energy. The resulting energy in joules is then displayed on the front panel as shown in step 510.

In summary, there has been provided a new and improved apparatus for assessing lethal ventricular tachyarrhythmia and in determining defibrillation thresholds. The subject invention advantageously combines a programmable stimulator with a defibrillator. The apparatus is provided with a number of features intended to improve operation, facilitating use by the physician and decreasing patient risk. Included in these improvements is an automatic charging circuit coupled with a dual channel capacitor defibrillator to substantially reduce the time to deliver a rescue shock if a test shock has failed. The subject system further includes ability to store multiple parameters enabling the unit to be pre-programmed prior to initiation of cardiac procedure. The unit also displays the energy and resistance present in a defibrillation shock. Finally, a display feature is also provided which gives information to the physician regarding the estimated energy of a pulse to be delivered having a specific voltage and pulse width.

While the above apparatus has been described with reference to a preferred embodiment, it should be apparent that various changes and modifications could be made therein by one skilled in the art without varying from the scope and spirit of the subject invention as defined by the appended claims.

We claim:

1. An improved processor controlled apparatus for stimulating the heart of a patient, said apparatus having a first circuit means for generating low voltage pacing pulses and a second circuit means for generating high voltage defibrillation pulses, with a first set of leads being provided for delivering the low voltage pacing pulses to the heart and with a second set of leads being connected to the second circuit means for delivering the high voltage defibrillation pulses to the heart said apparatus including a processor means, said apparatus further including a means for protecting the first circuit means from damage when the high voltage defibrillation pulses are delivered to the heart, the improvement comprising:

switch means connected between the first circuit means and the first set of leads said switch means being operable in response to a control signal from the processor means such that in a first condition said switch means is closed permitting said low voltage pacing pulses to be delivered to the heart via said first set of leads and in a second condition, said switch means is open to provide symmetric voltage protection to said first circuit means such that high voltage defibrillation pulses of either polarity generated by said second circuit means and delivered by said second set of leads will not reach said first circuit means or be shunted back to said patient via said first set of leads.

2. An apparatus as recited in claim 1 wherein said switch means includes a pair of transistors connected in series between said first circuit means and said first set of leads, said switch means further including a means for biasing said transistors in response to said control signal from said processor means.

3. An apparatus as recited in claim 2 wherein said biasing means includes an RF oscillator for receiving said control signal from said processor means and generating an RF signal in response thereto, said biasing means further including a pulse transformer and isolated gate drives connected between said RF oscillator and said transistors for supplying energy to the transistors, with said gate drives functioning to rectify the FR signal from the oscillator.

* * * * *